(12) United States Patent
Barbaux et al.

(10) Patent No.: US 9,309,552 B2
(45) Date of Patent: Apr. 12, 2016

(54) **METHOD FOR DETECTING *STREPTOCOCCUS AGALACTIAE* USING ESTERASE ACTIVITY**

(75) Inventors: Laurence Barbaux, Amberieux en Bugey (FR); Denis Robichon, Blyes (FR)

(73) Assignee: BIOMERIEUX, Marcy l'Etoile (FR)

( * ) Notice: Subject to any disclaimer, the term of this patent is extended or adjusted under 35 U.S.C. 154(b) by 942 days.

(21) Appl. No.: 11/660,386

(22) PCT Filed: Sep. 14, 2005

(86) PCT No.: PCT/FR2005/050739
§ 371 (c)(1),
(2), (4) Date: Feb. 16, 2007

(87) PCT Pub. No.: WO2006/032809
PCT Pub. Date: Mar. 30, 2006

(65) Prior Publication Data
US 2007/0254326 A1 Nov. 1, 2007

(30) Foreign Application Priority Data
Sep. 16, 2004 (FR) ...................................... 04 52068

(51) Int. Cl.
*C12N 9/00* (2006.01)
*C12Q 1/44* (2006.01)
*C12Q 1/14* (2006.01)
*C12Q 1/42* (2006.01)

(52) U.S. Cl.
CPC .. *C12Q 1/44* (2013.01); *C12Q 1/14* (2013.01); *C12Q 1/42* (2013.01)

(58) Field of Classification Search
CPC ....................................................... C12Q 1/14

USPC ............................................................ 435/19
See application file for complete search history.

(56) References Cited

U.S. PATENT DOCUMENTS

| 4,259,442 A | 3/1981 | Gayral |
| 4,603,108 A | 7/1986 | Bascomb |
| 5,962,251 A | 10/1999 | Rambach |
| 6,046,016 A * | 4/2000 | Orenga .......................... 435/24 |
| 6,387,650 B1 * | 5/2002 | Townsend et al. .............. 435/34 |
| 6,649,365 B1 * | 11/2003 | Orenga .......................... 435/24 |
| 7,691,601 B2 * | 4/2010 | Orenga et al. .................. 435/34 |
| 2002/0147317 A1 * | 10/2002 | Bentsen et al. .................... 536/8 |
| 2007/0020719 A1 * | 1/2007 | Duran Vila et al. ............. 435/34 |

FOREIGN PATENT DOCUMENTS

| CA | 1 322 733 C | 10/1993 |
| EP | 0 656 421 A1 | 6/1995 |
| EP | 0 881 284 A1 | 12/1998 |
| EP | 1 293 575 A2 | 3/2003 |
| FR | 2 708 286 A1 | 2/1995 |
| WO | WO 99/08207 A1 | 2/1999 |
| WO | WO 0240706 * | 5/2002 ............... C12Q 1/34 |

OTHER PUBLICATIONS

Motohiro, T. et al., "Pharmacokinetic and Clinical Studies on Cefpodoxime Proxetil Dry Syrup in the Field of Pediatrics," Japanese Journal of Antibiotics, vol. 42, No. 7, pp. 1629-1666, 1989.
Schrag, Stephanie et al., "Prevention of Prenatal Group B Streptococcal Disease, Revised Guidelines for CDC," Morbidity and Mortality Weekly Report, vol. 51, No. RR-11, Aug. 16, 2002.

* cited by examiner

*Primary Examiner* — Taeyoon Kim
*Assistant Examiner* — Tiffany Gough
(74) *Attorney, Agent, or Firm* — Oliff PLC

(57) ABSTRACT

The present invention concerns a method for specifically detecting and identifying *Streptococcus agalactiae*, using a reaction medium comprising at least one esterase enzymatic substrate.

5 Claims, No Drawings

METHOD FOR DETECTING *STREPTOCOCCUS AGALACTIAE* USING ESTERASE ACTIVITY

The present invention relates to the field of the detection and identification of *Streptococcus agalactiae*. More specifically, the invention relates to the use of esterase substrates, optionally in combination with at least one α-glucosidase substrate, phosphatase substrate, β-cellobiosidase substrate or N-acetylglucosaminidase substrate, for detecting and identifying *Streptococcus agalactiae*.

The *Streptococcus* genus contains numerous species that are very widespread in nature, on the skin and the mucous membranes of humans and animals, and are responsible for multiple infections. They are ubiquitous bacteria that are found in the free state in the outside environment (soil, air, water), in the saprophyte state or in the commensal state in humans and animals. They are located in the rhinopharynx for group A, C, G and H streptococci and *salivarius*, the intestine for group D fecal streptococci and the vaginal cavity for group B streptococci. Their pathogenic role is extremely varied and depends on the species in question and on their location in the organism.

Streptococci are Gram+cocci, 0.5 to 1 µm in diameter, that exhibit grouping in the form of a small chain and are immobile. They are catalase-negative, have a fermentative metabolism, and they are optionally anaerobic and are sensitive to variations in temperature (optimal growth 37° C.) and to variations in pH (optimal pH 7).

*Streptococcus agalactiae* (or streptococcus B) is recognized as one of the main infectious agents responsible for mastitis in cattle. In humans, it is essentially a saprophyte of the female genital tract (vagina), but it is also found in the rhinopharynx and in the intestine, in particular the rectum. In adults, colonization often remains asymptomatic, but *Streptococcus agalactiae* can be responsible for septicemia, pneumonia, meningitis, arthritis, urinary infections and deep suppurations. In women who are pregnant, or after having given birth, the infection may lead to endometritis and to sterility.

In newborns, the contamination occurs in utero or, most commonly, during birth, due to inhalation of the amniotic fluid or of vaginal secretions. An early infection often appears immediately after birth or within the first hours of life. Early infection is promoted by premature birth, rupture of the membranes and a strong colonization of the mother's vagina. The mortality rate in this type of infection is very high (>50%). Late infections are generally reflected by meningitis (infantile meningitis) and arthritis.

Systematic screening for the carrying of *Streptococcus agalactiae* is recommended at the end of pregnancy, ideally between 34 and 38 weeks of amenorrhea (35-37 weeks of pregnancy), due in particular to its prevalence (10% in France, i.e. at least 75 000 pregnant women/year) and to the consequences thereof during full-term births, which makes it a public health problem.

Selective media and/or media which make it possible to direct the diagnosis are commercially available. However, these media have the drawback that they are not sufficient on their own for the diagnosis of *Streptococcus agalactiae* and that it is necessary to carry out supplementary tests, such as demonstrating group B Lancefield antigen (polysaccharide with dominant presence of rhamnose) and hippurate hydrolysis (hippurate broth).

The selective media most commonly used are Todd-Hewitt broth, an enrichment broth for searching for group B streptococci in pregnant women. This broth contains various antibiotics that inhibit most Gram-negative microorganisms of the accompanying flora, such as nalixidic acid and gentamycin, or nalixidic acid, polymyxin and crystal violet.

After the enrichment step, the antibiotic-supplemented Todd-Hewitt broth must be subcultured on media for searching for streptococci (see CDC (Center for Disease Control) recommendations, MMWR (Morbidity and Mortality Weekly Report), 16 Aug. 2002, Vol. 51, No. RR-11).

Lim medium is a variant of Todd-Hewitt broth and it contains 1% of yeast extract, nalixidic acid and colistin.

A Columbia agar containing 5% of blood is also used and makes it possible in particular to demonstrate the β-hemolytic characteristic of *Streptococcus agalactiae*. However, this characteristic is not always apparent: the hemolytic halo around the colonies may be narrow, giving rather the α-hemolytic, or even γ-hemolytic, appearance. On the other hand, this characteristic becomes clear if, in the area of the *Streptococcus agalactiae* colonies, there are *Staphylococcus aureus* colonies (Camp-factor).

The drawbacks of these selective media are that they must be supplemented with biochemical tests and/or immunoassays.

Currently, the only commercially available, ready-to-use selective medium that makes it possible to directly isolate and identify *Streptococcus agalactiae* from rectovaginal samples is Granada medium (Biolys SA). This medium has the characteristic of promoting the production of a carotenoid pigment by *Streptococcus agalactiae* strains due to the presence in the medium of soluble starch, proteose peptone No. 3, glucose, sodium pyruvate, magnesium sulfate, methotrexate, colistin, crystal violet, agar, horse serum, anhydrous $Na_2HPO_4$, metronidazole, MOPS (morpholinopropanesulfonic acid) hemi-sodium salt and distilled water, and incubation under anaerobic conditions. This medium therefore has the drawback that the direct detection of *Streptococcus agalactiae* is carried out under anaerobic conditions, which is not easy to implement. Moreover, no detection medium containing one or more enzymatic substrates is available.

The applicant has now demonstrated, against all expectations, that it is possible to use enzymatic substrates, in particular esterase enzymatic substrates, for specifically detecting and identifying *Streptococcus agalactiae*.

Specifically, surprisingly, the applicant has demonstrated that only *Streptococcus agalactiae*, among the closest bacterial species most commonly encountered in an associated manner, are incapable of using esterase enzymatic substrates early on (at less than 18 h after inoculation), such that they are the only ones not to be revealed early on by esterase substrates, for example with no modification of the colonies being obtained in the medium early on, for example with no modification of the coloration of the colonies being obtained in the medium when a chromogenic esterase substrate is used, without there being any diffusion of the coloration in the reaction medium, and therefore with the coloration being concentrated at the colonies, without these molecules having, however, a harmful effect on the growth of the bacteria.

Consequently, this enzymatic substrate has the additional advantage that the results can be read early, in particular at approximately 18-20 h of incubation, with a very good contrast.

Thus, a subject of the present invention is a method for specifically detecting and identifying *Streptococcus agalactiae*, characterized in that a reaction medium comprising at least one esterase enzymatic substrate is used.

The esterase enzymatic substrates that are suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com, or in the GLYCOSYNTH catalog, enzyme substrates catalog or www.glycosynth.co.uk.

By way of example of esterase substrates, mention may be made of indoxyloctanoate, indoxylnonanoate or indoxyldecanoate derivatives, preferably indoxyloctanoate derivatives, more preferably their halogenated derivatives, more preferably the chlorinated or brominated derivatives such as 5-bromo-6-chloro-3-indoxyloctanoate and 5-bromo-4-chloro-3-indoxyloctanoate for which the reading is particularly early.

Since a slight esterase activity is observed after 24 h of incubation (activity less than 0.6 on a scale of 0 to 4), the detection of *Streptococcus agalactiae* can be improved by adding at least one other enzymatic substrate. Due to the specific property of *Streptococcus agalactiae* of not using the esterase substrate, or of using it very little, it makes no difference whether or not the other enzymatic substrate is used by *Streptococcus agalactiae* and the other species. In addition, since the use of the esterase substrate by *Streptococcus agalactiae* is only very slight, such that this only slightly modifies the appearance of the colonies obtained, we will indicate, in the subsequent text, only that *Streptococcus agalactiae* are incapable of using the esterase substrate.

Thus, according to one embodiment, the method of the invention uses a reaction medium also comprising another enzymatic substrate other than an esterase substrate.

The enzymatic substrates other than an esterase substrate (non-esterase substrate) suitable for the purposes of the invention are any substrate of which the use by a strain confers on the colony an appearance different than the appearance obtained when the esterase substrate is used. Such a different appearance is, for example, a different coloration. Moreover, this non-esterase substrate is such that, when a strain uses both this non-esterase substrate and the esterase substrate (strain other than *Streptococcus agalactiae*), the appearance of the colonies obtained (for example, their coloration) is also different than the appearance of the colonies of *Streptococcus agalactiae*. Specifically, when both an esterase substrate and a non-esterase substrate that can be used by the *Streptococcus agalactiae* strains are combined in a reaction medium, the *Streptococcus agalactiae* strains are then negative for the esterase and positive for the non-esterase substrate (they can be marked −/+, the first part of the equation corresponding to the esterase substrate and the second part corresponding to the non-esterase substrate), while the other strains are capable of using either only the esterase substrate (they are +/−), or both the esterase substrate and the non-esterase substrate (they are +/+). Similarly, when both an esterase substrate and a non-esterase substrate that cannot be used by the *Streptococcus agalactiae* strains are combined in a reaction medium, the *Streptococcus agalactiae* strains are then negative for the esterase and negative for the non-esterase substrate (they are −/−), while the other strains are capable of using either only the esterase substrate (they are +/−), or both the esterase substrate and the non-esterase substrate (they are +/+). In summary, the *Streptococcus agalactiae* strains are always −/+ or −/−, whereas the other species are always +/− or +/+.

Thus, for example, if a chromogenic esterase substrate which results in a blue coloration of the colonies when the colony under consideration uses the substrate is combined with another chromogenic enzymatic substrate which results in a pink coloration of the colonies when the colony under consideration uses the substrate, four types of coloration can be obtained: either pink, or colorless to slightly blue, or blue, or violet (pink+blue). The pink coloration and the colorless to slightly blue appearance are only representative of *Streptococcus agalactiae* as follows: either the strain is capable of using the non-esterase substrate and the colony becomes pink (−/+ strain), or it is incapable of using the non-esterase substrate and the colony remains colorless or becomes slightly blue (−/− strain). The blue and violet colorations are representative of the other species as follows: either the strain is capable only of using the esterase substrate and it becomes blue (+/− strain), or the strain is capable of using both the esterase substrate and the other enzymatic substrate and it becomes pink and blue, i.e. violet (+/+ strain).

Similarly, if a fluorescence-absorbing esterase substrate, which results in quenching of fluorescence when the colony under consideration uses the substrate, is combined with another fluorescent enzymatic substrate which results in fluorescence at the colonies when the colony under consideration uses the substrate, the latter substrate being used by *Streptococcus agalactiae*, two types of colonies can be obtained: either fluorescent colonies, or weakly to non-fluorescent colonies. The fluorescent colonies are representative only of *Streptococcus agalactiae* since this species is only capable of using the enzymatic substrate other than the esterase substrate. The weakly to non-fluorescent colonies are representative of the other species as follows: either the strain is only capable of using the esterase substrate and it is non-fluorescent, or the strain is capable of using both the esterase substrate and the other enzymatic substrate and it is weakly to non-fluorescent.

Examples of such substrates other than an esterase substrate that are suitable for the purposes of the invention include α-glucosidase substrates, phosphatase substrates, β-cellobiosidase substrates, N-acetylglucosaminidase substrates and β-glucosidase substrates.

Thus, according to another embodiment, the method of the invention uses, as reaction medium, a reaction medium comprising, in addition to an esterase substrate, at least one enzymatic substrate chosen from α-glucosidase substrates, phosphatase substrates, β-cellobiosidase substrates, N-acetylglucosaminidase substrates and β-glucosidase substrates.

The reaction media comprising or consisting of an esterase substrate and (of) at least one enzymatic substrate chosen from an α-glucosidase substrate, a phosphatase substrate and a β-cellobiosidase substrate are novel and constitute another subject of the invention.

The α-glucosidase enzymatic substrates suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com, or in the GLYCOSYNTH catalog, enzyme substrates catalog or www.glycosynth.co.uk.

By way of example of an α-glucosidase substrate, mention may be made of indoxyl-derivative-based substrates, umbelliferone-derivative-based substrates and naphthol-derivative-based substrates.

Preferably, the α-glucosidase enzymatic substrate suitable for the purposes of the invention is an indoxyl-derivative-based substrate.

Examples of such indoxyl derivatives include derivatives of 3-indolyl-α-D-glucopyranoside, preferably halogenated derivatives of these compounds. By way of examples of halogenated 3-indolyl-α-D-glucopyranoside derivatives, mention may be made of 6-bromo-3-indolyl-α-D-glucopyranoside, 5-bromo-6-chloro-3-indolyl-α-D-glucopyranoside, 5-bromo-4-chloro-3-indolyl-α-D-glucopyranoside,
5-bromo-4-chloro-3-indolyl-N-méthyl-α-D-glucopyranoside and 6-chloro-3-indolyl-α-D-glucopyranoside, the latter compound being particularly preferred.

The phosphatase enzymatic substrates suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com.

By way of example of a phosphatase substrate, mention may be made of indolyl-derivative-based substrates, umbelliferone-derivative-based substrates and nitrophenyl-based substrates.

Preferably, the phosphatase enzymatic substrate suitable for the purposes of the invention is an indoxyl-derivative-based substrate.

Examples of such indoxyl derivatives include 3-indolyl phosphate derivatives such as 5-bromo-4-chloro-3-indolyl phosphate, 5-bromo-6-chloro-3-indolyl phosphate and 6-chloro-3-indolyl phosphate, the latter compound being particularly preferred.

The β-cellobiosidase enzymatic substrates suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com or in the GLYCOSYNTH catalog, enzyme substrates catalog or www.glycosynth.co.uk.

By way of example of β-cellobiosidase substrate, mention may be made of indolyl-derivative-based substrates, umbelliferone-derivative-based substrates and nitrophenyl-based substrates.

Preferably, the β-cellobiosidase enzymatic substrate suitable for the purposes of the invention is an indoxyl-derivative-based substrate.

Examples of such indoxyl derivatives include 3-indolyl-β-D-cellobioside derivatives such as 6-chloro-3-indolyl-☐-D-cellobioside and 5-bromo-4-chloro-3-indolyl-β-D-cellobioside, the latter compound being particularly preferred.

The N-acetylglucosaminidase enzymatic substrates suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com or in the GLYCOSYNTH catalog, enzyme substrates catalog or www.glycosynth.co.uk.

By way of example of an N-acetylglucosaminidase substrate, mention may be made of indoxyl-derivative-based substrates, umbelliferone-derivative-based substrates and nitrophenyl-based substrates.

Preferably, the N-acetylglucosaminidase enzymatic substrate suitable for the purposes of the invention is an indoxyl-derivative-based substrate.

Examples of such indoxyl derivatives include 3-indolyl-β-N-acetyl-glucosaminide derivatives such as 5-bromo-6-chloro-3-indolyl-N-acetyl-β-D-glucosaminide, 6-chloro-3-indolyl-N-acetyl-β-D-glucosaminide and 5-bromo-4-chloro-3-indolyl-β-N-acetylglucosaminide, the latter compound being particularly preferred.

The β-glucosidase enzymatic substrates suitable for the purposes of the invention are any substrate known to those skilled in the art that makes it possible to demonstrate such an enzymatic activity. Such substrates may, for example, be chromogenic or fluorescent and are described, for example, in the BIOSYNTH catalog, Substrates and Reagents or www.biosynth.com or in the GLYCOSYNTH catalog, enzyme substrates catalog or www.glycosynth.co.uk.

By way of example of a β-glucosidase substrate, mention may be made of indolyl-derivative-based substrates, umbelliferone-derivative-based substrates and nitrophenyl-based substrates.

Preferably, the β-glucosidase enzymatic substrate suitable for the purposes of the invention is an indoxyl-derivative-based substrate.

Examples of such indoxyl derivatives include 3-indolyl-β-D-glucopyranoside derivatives such as 5-bromo-4-chloro-3-indolyl-β-D-glucopyranoside, 5-bromo-6-chloro-3-indolyl-β-D-glucopyranoside, 6-chloro-3-indolyl-β-D-glucopyranoside and 5-bromo-4-chloro-3-indolyl-N-methyl-β-D-glucopyranoside.

According to one embodiment, the method of the invention uses a reaction medium comprising i) an esterase substrate and ii) a phosphatase substrate or an α-glucosidase substrate, the esterase substrate/phosphatase substrate combination being preferred.

According to another embodiment, the reaction medium comprises, in addition to the esterase substrate and the phosphatase substrate or α-glucosidase substrate, an enzymatic substrate chosen from a β-cellobiosidase substrate, an N-acetylglucosaminidase substrate and a β-glucosidase substrate, preferably a β-cellobiosidase substrate and an N-acetylglucosaminidase substrate.

The reaction medium as used in the method of the invention is therefore a detection reaction medium due to the presence of at least one enzymatic substrate.

This reaction medium can either be used as a visualization medium only, or as a culture and visualization medium. In the first case, the culturing of the microorganisms is carried out before inoculation and, in the second case, the reaction medium also constitutes the culture medium.

The reaction medium may be solid, semi-solid or liquid. The term "solid or semi-solid medium" is intended to mean, for example, a gelled medium.

Agar is the conventional solid medium in microbiology for culturing microorganisms, but it is possible to use gelatin or agarose. A certain number of preparations are commercially available, for instance Columbia agar, trypcase-soy agar, MacConkey agar, Sabouraud agar or, more generally, those described in the Handbook of Microbiological Media (CRC Press).

The amount of agar in the reaction medium is from 2 to 40 g/l. For the solid media, the amount of agar is preferably from 9 to 25 g/l, more preferably from 12 to 14 g/l. For the semi-solid media, the amount of agar is preferably from 2 to 6 g/l.

The enzymatic substrates of the invention can be used in a wide pH range, in particular between pH 5.5 and 10.

The concentration of the enzymatic substrate(s) in the reaction medium is between 10 and 2000 mg/l, preferably between 50 and 500 mg/l, more preferably between 80 and 400 mg/l, which constitutes a preferred embodiment of the invention.

Of course, those skilled in the art will determine the concentration of the enzymatic substrate(s) in the medium within this range, according to the substrate chosen. Thus, insofar as the esterase substrate used is 5-bromo-4-chloro-3-indyloctanoate, a concentration of between 100 and 400 mg/l is preferred.

The reaction medium that can be used for the purposes of the invention may also comprise other components that are of use for improving the specificity and/or the sensitivity of the method of the invention.

Thus, according to one embodiment of the invention, the reaction medium comprises phosphate solutions such as Na$_2$HPO$_4$ and K$_2$HPO$_4$ solutions.

This is because the use of such phosphate solutions makes it possible to substantially improve the readability of the medium, which is reflected either by a strength in coloration sharpness, or by an increase in the expression and/or in the detection of the phosphatase activity at 18 h.

The concentration of such phosphate solutions is between 0.3 and 1.5 g/l for each solution, a concentration of 0.5 g/l being preferred.

The reaction medium may also contain a mixture of inhibitors for inhibiting or limiting the growth of unwanted strains, such as false-positive strains, for example *Candida* or *Staphylococcus saprophyticus*, without modifying the detection sensitivity of the medium.

In this respect, the reaction mixture may contain a mixture of antibiotics. The addition of antibiotics to the reaction medium allows, inter alia, a time to be saved since the identification of *Streptococcus agalactiae* is carried out directly.

Examples of antibiotics that are suitable for the purposes of the invention include aztreonam and amphotericin B. These antibiotics are commercially available from ICN, Squibb or Sigma.

The amount of each antibiotic in the reaction medium varies according to the antibiotic concerned, and will be readily determined by those skilled in the art.

The reaction medium may also comprise one or more elements in combination, such as amino acids, peptones, carbohydrates, nucleotides, minerals, vitamins, surfactants, buffers, phosphate salts, ammonium salts, sodium salts or metal salts. Examples of media are described in the applicant's patent applications EP 656 421 and WO 99/09207.

The implementation of the method of the invention can be carried out according to the following steps consisting in:
a) inoculating a reaction medium as defined above, with all or part of the sample,
b) incubating the inoculated medium,
c) revealing the presence of at least one esterase activity alone or in combination with at least one other enzymatic activity other than an esterase activity, which constitutes another subject of the invention.

The inoculation and incubation steps are widely known to those skilled in the art.

For example, the incubation temperature may be 37° C. As regards the incubation atmosphere, it is preferably aerobic.

The revealing is carried out with the naked eye by visualization of a change in coloration that does not diffuse in the reaction medium and is therefore concentrated at the colonies. In the case of the revealing of the fluorescence, the fluorescence reading devices known to those skilled in the art are used.

The biological samples to be analyzed are any clinical sample liable to contain *Streptococcus agalactiae*, such as a vaginal specimen, a urine specimen or any other sample of which the analysis may aid a clinician in reaching a diagnosis.

The invention will be understood more clearly from the following examples given by way of nonlimiting illustration.

Example 1

Detection of *Streptococcus agalactiae* Using Esterase Enzymatic Substrates 1.1 Preparation of the Reaction Media The reaction media were prepared by mixing heart-brain extract (4.84 g/l; Solabia), meat infusion (1.96 g/l; Solabia), biothione (1 g/l; Solabia), biotrypcase (7.2 g/l; Solabia), sodium carbonate (0.3 g/l; VWR), sodium pyruvate (2 g/l; Fluka), HEPES buffer (0.4 g/l; Sigma), lactalbumin peptone (2 g/l; DMV), glucose (1 g/l; Merck), American agar (2 g/l; Sobigel) and European agar (12 g/l; Roko).

After autoclaving for 15 min at 121° C., an esterase enzymatic substrate as indicated below was added at a rate of 0.3 g/l; followed by cooling in a water bath at 50° C.:
5-bromo-4-chloro-3-indolyloctanoate (X-C8; Inalco), which gives a turquoise coloration when it is used, and
5-bromo-6-chloro-3-indolyloctanoate (Magenta-C8; Inalco), which gives a pink-red coloration when it is used.

The media were then poured into a Petri dish for the subsequent inoculation with bacterial strains.

1.2 Inoculation of the Microorganism Strains

Three *Streptococcus agalactiae* strains and three strains of other bacteria, all from the applicant's collection, suspended in physiological saline, were inoculated so as to give isolated colonies on each of the media. The dishes were incubated at 37° C. for 48 hours. The colonies formed were examined visually after 18, 24 and more than 40 hours of incubation. The coloration of these colonies, the growth and also the intensity of this coloration (representative of the esterase activity) were noted.

1.3 Results

The results are given in Table 1 hereinafter and are expressed:
in terms of growth (G) with the size being indicated in mm,
in terms of color (Co) with T=turquoise, R=pink or red,
in terms of intensity (I) of coloration, based on an arbitrary scale ranging from 0 to 4, 0 corresponding to an absence of activity and 4 corresponding to the presence of a very intense coloration,
according to the incubation time in hours (T).

TABLE 1

| Strains | | X-C8 | | | Magenta-C8 | | |
| --- | --- | --- | --- | --- | --- | --- | --- |
| (accession No.) | T | G | Co | I | G | Co | I |
| Streptococcus | 18 | 1.2 | | | 1.2 | | |
| agalactiae | 24 | 2 | T | 0.3 | 2 | R | 0.3 |
| (7611003) | >40 | 2.5 | T | 2.3 | 2.5 | R | 1.7 |
| Streptococcus | 18 | 0.4 | | | 0.4 | | |
| agalactiae | 24 | 0.7 | T | 0.3 | 0.7 | R | 0.3 |
| (0101060) | >40 | 1.3 | T | 3 | 1.3 | R | 2 |
| Streptococcus | 18 | | | | 0.3 | | |
| agalactiae | 24 | 0.2 | | | 0.5 | | |
| (8904053) | >40 | 0.3 | T | 0.3 | 1 | | |
| Enterococcus | 18 | 0.8 | T | 1.7 | 0.8 | R | 1 |
| faecalis | 24 | 2 | T | 3 | 1.8 | R | 1.7 |
| (0008192) | >40 | 2 | T | 3.5 | 2 | R | 3.5 |
| Enterococcus | 18 | 0.5 | T | 2 | 0.7 | R | 1 |
| faecium | 24 | 1 | T | 3 | 1.7 | R | 2.7 |
| (7611005) | >40 | 1 | T | 3 | 1.7 | R | 3 |
| Staphylococcus | 18 | 0.5 | T | 2 | 0.5 | R | 2 |
| epidermidis | 24 | 1.5 | T | 3 | 1 | R | 3 |
| (7509009) | >40 | 1.5 | T | 3 | 1.3 | R | 3.5 |

The results demonstrate that streptococci B can be detected early using an esterase enzymatic substrate since they exhibit a zero to very weak activity at 18-24 h.

Example 2

Detection of *Streptococcus agalactiae* Using an Esterase Substrate and an α-glucosidase Substrate or Phosphatase Substrate The protocol described above in Example 1 was repeated, with the exception that, at the same time as 0.3 g/l of the esterase substrate X-C8, 0.3 g/l of 6-chloro-3-indolyl-α-D-glucopyranoside (Rose-α-Glu), or 0.3 g/l of 6-chloro-3-indolyl phosphate (Rose-P), which give a pink coloration when they are used, was added.

The results are given in Table 2 below, in which the growth, the coloration and the intensity are given, as in Example 1, and where R=Pink/(Rose)/Red, PB=Pink-Brown, T=Turquoise, Gr=Green, Vi=Violet, B=Blue, GVi=Grey-Violet and GB=Grey-Blue.

TABLE 2

| Strains | | X-C8 + Rose-alpha-Glu | | | X-C8 + Rose-P | | |
|---|---|---|---|---|---|---|---|
| (accession No.) | T | G | Co | I | G | Co | I |
| Streptococcus | 18 | 1.3 | R | 3 | 1 | R | 3 |
| agalactiae | 24 | 1.3 | R | 3 | 1.7 | R | 4 |
| (7611003) | >40 | 2 | R | 4 | 2 | R | 4 |
| Streptococcus | 18 | 0.2 | R | 2 | 0.5 | R | 3 |
| agalactiae | 24 | 0.3 | R | 2 | 0.5 | R | 3.5 |
| (8709013) | >40 | 1 | R | 4 | 1.7 | R | 4 |
| Streptococcus | 18 | 1 | R | 2 | 0.8 | R | 3 |
| agalactiae | 24 | 1.7 | PB | 2.7 | 1.3 | R | 4 |
| (7702055) | >40 | 1.7 | R | 4 | 1.7 | R | 4 |
| Enterococcus | 18 | 1.5 | T | 3 | 1.7 | GB | 3 |
| faecium | 24 | 1.7 | T | 3 | 1.7 | B | 3.5 |
| (7611005) | >40 | 1.8 | T | 4 | 2 | GVi | 4 |
| Staphylococcus | 18 | 0.7 | Gr | 3 | 0.6 | GVi | 3.5 |
| epidermidis | 24 | 1.3 | GB | 3.5 | 1.3 | GVi | 3.5 |
| (7509009) | >40 | 1.3 | GB | 3.5 | 1.5 | GVi | 4 |
| Staphylococcus | 18 | 3 | GVi | 4 | 3 | Vi | 4 |
| aureus | 24 | 3 | Vi | 4 | 3 | Vi | 4 |
| (9202070) | >40 | 3 | Vi | 4 | 3 | Vi | 4 |

This table demonstrates that the detection of the *Streptococcus agalactiae* strains is improved when a chromogenic esterase substrate is used in combination with another chromogenic enzymatic substrate, other than an esterase substrate, that can be used by the *Streptococcus agalactiae* strains.

Example 3

Detection of *Streptococcus agalactiae* Using an Esterase Substrate, a Phosphatase Substrate and a β-cellobiosidase Substrate The protocol described in Example 2 was repeated, using 0.3 g/l of X-C8 and 0.2 g/l of Rose-P, with the exception that 0.08 g/l of 5-bromo-4-chloro-3-indolyl-β-D-cellobioside (Cellobio) is also added at the same time as the other substrates, along with 0.5 g/l of Na$_2$HPO$_4$ and 0.5 g/l of K$_2$HPO$_4$, before autoclaving.

As control medium, a medium with only X-C8 and Rose-P was used.

The results are given in Table 3 below, in which the growth, the coloration and the intensity are given, as in Example 1, and where R=Pink/Rose)/Red, Ma=Mauve, Vi=Violet, B=Blue, GB=Grey-Blue and DP=Dark Purple.

TABLE 3

| Strains | | Control | | | X-C8 + Rose-P + Cellobio | | |
|---|---|---|---|---|---|---|---|
| (accession No.) | T | G | Co | I | G | Co | I |
| Streptococcus | 18 | 0.7 | R | 1.7 | 0.7 | R | 1.3 |
| agalactiae | 24 | 0.7 | R | 4 | 0.7 | R | 3 |
| (0101060) | >40 | 1.5 | R | 4 | 1.5 | R | 4 |
| Streptococcus | 18 | 1.3 | R | 4 | 1 | R | 4 |
| agalactiae | 24 | 1.5 | R | 4 | 1.5 | R | 4 |
| (7701031) | >40 | 1.5 | R | 4 | 1.5 | R | 4 |
| Streptococcus | 18 | 1 | R | 2 | 1 | R | 2 |
| agalactiae | 24 | 1.5 | R | 4 | 1.5 | R | 4 |
| (7702055) | >40 | 1.7 | R | 4 | 1.7 | R | 4 |

TABLE 3-continued

| Strains | | Control | | | X-C8 + Rose-P + Cellobio | | |
|---|---|---|---|---|---|---|---|
| (accession No.) | T | G | Co | I | G | Co | I |
| Streptococcus | 18 | 0.3 | | | 0.3 | B | 0.5 |
| anginogus | 24 | 0.5 | R | 0.1 | 0.4 | B | 1.3 |
| (8507046) | >40 | 1 | R | 2.3 | 1 | B | 2.7 |
| Enterococcus | 18 | 1.5 | Ma | 1.7 | 1.3 | B | 3 |
| faecium | 24 | 1.7 | Ma | 3 | 1.5 | GB | 4 |
| (0002043) | >40 | 2 | DP | 4 | 2 | DP | 4 |

The results in Table 3 demonstrate an improvement in the specificity of detection of *Streptococcus agalactiae* compared with the other strains when three enzymatic substrates, including an esterase substrate, are used.

Example 4

Detection of *Streptococcus agalactiae* Using an Esterase Substrate, a Phosphatase Substrate and an N-acetylglucosaminidase Substrate The protocol described in Example 3 was repeated, with the exception that 0.4 g/l of 5-bromo-4-chloro-3-indolyl-β-N-acetylglucosaminide (X-NAGlu) was used in place of the Cellobio.

The control medium is identical to the medium tested, with the exception that it does not contain any X-NAGlu.

The results are given in Table 4 below, in which the growth, the coloration and the intensity are given, as in Example 1, and where R=Pink/Red, B=Blue, GP=Grey-Pink and Mg=Magenta.

TABLE 4

| Strains | | Control | | | X-C8 + Rose-P + X-NAGlu | | |
|---|---|---|---|---|---|---|---|
| (accession No.) | T | G | Co | I | G | Co | I |
| Streptococcus | 18 | 0.5 | R | 3 | 0.5 | R | 2.3 |
| agalactiae | 24 | 1 | R | 4 | 1 | R | 3 |
| (7611003) | >40 | 1.2 | R | 4 | 1.2 | R | 4 |
| Streptococcus | 18 | 0.5 | R | 2.7 | 0.5 | R | 2.7 |
| agalactiae | 24 | 0.7 | R | 4 | 0.7 | R | 4 |
| (7701031) | >40 | 0.7 | R | 4 | 0.7 | R | 4 |
| Enterobacter | 18 | 1.7 | R | 2.3 | 1.7 | GP | 2 |
| clocae | 24 | 2 | R | 3 | 2 | B | 3 |
| (0010003) | >40 | 2.5 | B | 4 | 3 | B | 4 |
| Enterococcus | 18 | 0.5 | GP | 2 | 0.5 | B | 3 |
| faecium | 24 | 0.8 | GP | 2.7 | 0.8 | B | 3.5 |
| (0002043) | >40 | 1 | Mg | 4 | 1 | B | 4 |

The results in this table demonstrate an improvement in the specificity of detection of *Streptococcus agalactiae* compared with the other strains when three enzymatic substrates, including an esterase substrate, are used.

Example 5

Detection of *Streptococcus agalactiae* Using an Esterase Substrate, a Phosphatase Substrate and a β-glucosidase Substrate The protocol described in Example 4 was repeated, with the exception that 0.08 g/l of 5-bromo-4-chloro-3-indolyl-β-D-glucopyranoside (X-β-Glu) and 0.3 g/l of 5-bromo-4-chloro-3-indolyl-N-methyl-β-D-glucopyranoside (GreenA-β-Glu) were used in place of the X-NAGlu.

The control medium is identical to the medium tested, with the exception that it does not contain any X-β-Glu or GreenA-β-Glu.

The results are given in Table 5 below, in which the growth, the coloration and the intensity are given, as in Example 1, and where R=Pink/Red, Ma=Mauve, Vi=Violet, B=Blue and GB=Grey-Blue.

TABLEAU 5

| Strains (accession No.) | | Control | | | X-C8 + Rose-P + X-β-Glu | | | X-C8 + Rose-P + GreenA-β-Glu | | |
|---|---|---|---|---|---|---|---|---|---|---|
| | T | G | Co | I | G | Co | I | G | Co | I |
| Streptococcus | 18 | 0.4 | | | 0.3 | | | 0.2 | | |
| agalactiae | 24 | 0.5 | R | 0.5 | 0.5 | R | 0.3 | 0.4 | R | 0.3 |
| (9001001) | >40 | 1.7 | R | 4 | 1.3 | R | 4 | 1.5 | R | 4 |
| Streptococcus | 18 | 1.3 | R | 4 | 1.3 | R | 4 | 1 | R | 4 |
| agalactiae | 24 | 1.5 | R | 4 | 1.5 | R | 4 | 1.5 | R | 4 |
| (7701031) | >40 | 1.5 | R | 4 | 1.5 | R | 4 | 1.5 | R | 4 |
| Streptococcus | 18 | 1 | R | 2 | 1 | R | 2 | 1 | R | 2 |
| agalactiae | 24 | 1.5 | R | 4 | 1.5 | R | 4 | 1.3 | R | 4 |
| (7702055) | >40 | 1.7 | R | 4 | 1.7 | R | 4 | 1.5 | R | 4 |
| Streptococcus | 18 | 0.3 | | | 0.3 | B | 3 | 0.3 | B | 0.5 |
| anginogus | 24 | 0.5 | R | 0.1 | 0.4 | B | 4 | 0.4 | B | 2 |
| (8507046) | >40 | 1 | R | 2.3 | 1 | B | 4 | 1 | B | 3.5 |
| Enterococcus | 18 | 1.5 | Ma | 1.7 | 1.5 | B | 4 | 1.5 | GB | 4 |
| Faecium | 24 | 1.7 | Ma | 3 | 1.5 | B | 4 | 1.7 | GB | 4 |
| (0002043) | >40 | 2 | Vi | 4 | 2 | B | 4 | 2 | GB | 4 |

The results obtained in Table 5 demonstrate an improvement in the specificity of detection of *Streptococcus agalactiae* compared with the other strains when three enzymatic substrates, including an esterase substrate, are used.

Example 6

Improvement in the Sensitivity of Detection by Adding Phosphate Solution

The protocol described in Example 1 was repeated, with the exception that 0.3 g/l of Rose-P and also 0.5 g/l of $Na_2HPO_4$ and 0.5 g/l of $K_2HPO_4$ were added at the same time as 0.3 g/l of the esterase substrate X-C8.

The same medium, but with no phosphate solution, was used as control medium.

The results are given in Table 6 below, in which the growth, the coloration and the intensity are given, as in Example 1, where R=Pink and Mg=Magenta.

TABLE 6

| Strains (accession No.) | | Control | | | Medium with phosphate solution | | |
|---|---|---|---|---|---|---|---|
| | T | G | Co | I | G | Co | I |
| Streptococcus | 18 | 1.3 | R | 3 | 1.3 | Mg | 3.5 |
| agalactiae | 24 | 1.7 | Mg | 4 | 1.7 | Mg | 4 |
| (7611003) | >40 | 1.8 | Mg | 4 | 1.8 | Mg | 4 |
| Streptococcus | 18 | 0.4 | R | 0.5 | 0.5 | Mg | 3 |
| agalactiae | 24 | 0.5 | Mg | 4 | 0.7 | Mg | 3.5 |
| (0101060) | >40 | 1.5 | Mg | 4 | 1.5 | Mg | 4 |
| Streptococcus | 18 | 1 | Mg | 3 | 1 | R | 3.5 |
| agalactiae | 24 | 1.5 | Mg | 4 | 1.5 | Mg | 4 |
| (7702055) | >40 | 1.5 | Mg | 4 | 1.5 | Mg | 4 |

The results in this Table 6 demonstrate an improvement in the sharpness of coloration from 18 h, or an increase in the expression of the *S. agalactiae* strains.

Example 7

Comparison of the Sensitivity and the Specificity of Detection of *S. agalactiae* Using a Medium Containing an Esterase Substrate According to the Invention and the Commercially Available Media For this sensitivity and specificity study, a medium according to the invention, prepared as described in Example 1, containing 0.3 g/l of X-C8 and also: 0.2 g/l of Rose-P, 0.08 g/l of Cellobio, 0.5 g/l of $Na_2HPO_4$, 0.5 g/l of $K_2HPO_4$, 0.012 g/l of aztreonam and 0.004 g/l of amphotericin B, was used.

As medium for comparison, the Granada medium (ref. 10 077, BIOLYS, France) (Granada medium) was used.

69 strains of microorganisms, including 14 of *Streptococcus agalactiae*, were inoculated and left to incubate at 37° C. for up to 24 h and at ambient temperature beyond this time. The colonies were visualized as described above. The confirmation of the colonies suspected of being characteristic of streptococcus B, i.e. appearing to be pink/red, was carried out by means of an agglutination assay using the Slidex Strepto Kit reagent according to the supplier's recommendations (bioMérieux, France). The non-characteristic colonies, i.e. the colonies that were other than pink or that had the characteristic coloration but gave a negative response in the agglutination assay (false-positive strains), were identified by means of Galeries ID 32 Strep (bioMérieux, France).

The results are expressed as % of correct diagnosis relative to all the tests in terms of sensitivity and specificity, and are given in Table 7 below, the % sensitivity corresponding to the number of true positives detected on the medium divided by the total number of true positives to be detected (*100), and the % specificity corresponding to the number of true negatives detected on the medium divided by the total number of true negatives to be detected (*100).

TABLE 7

| | % sensitivity and specifity of detection of *S. agalactiae* | | | | | |
|---|---|---|---|---|---|---|
| | Granada medium | | | Medium of the invention | | |
| | 18 h | 24 h | >40 h | 18 h | 24 h | >40 h |
| Sensitivity without enrichment | 50 | 50 | 50 | 79 | 79 | 93 |
| Sensitivity with enrichment | 50 | 50 | 50 | 79 | 86 | 93 |
| Specificity without enrichment | 100 | 100 | 100 | 87 | 82 | 80 |
| Specificity with enrichment | 100 | 100 | 100 | 89 | 93 | 82 |

The results indicated in this table demonstrate the improvement in the sensitivity of detection of streptococci B (*Streptococcus agalactiae*) using the method of the invention. Moreover, they also demonstrate that the detection medium of the invention also has good specificity, which specificity is improved after enrichment due to a passage in Todd-Hewitt broth for 18-24 hours at 35-37° C. with or without 5% $CO_2$ before inoculation of the agar (see CDC (Center for Disease Control) recommendations, MMWR (Morbidity and Mortality Weekly Report), 16 Aug. 2002, Vol. 51, No. RR-11).

Example 8

Use of the Medium Based on Clinical Samples

For this study, the medium according to the invention, as prepared as described above in Example 7, was used.

A total of 134 samples/swabs originating from vaginal or endocervical specimens from pregnant women were used in this study.

Each swab was emulsified in 1 ml of sterile physiological saline and 100 μl of this solution were deposited, firstly, onto a Columbia agar containing 5% of horse blood, and, secondly, onto the medium used in the method of the invention. Moreover, 100 μl of the above solution were used to inoculate a Todd Hewitt broth. After incubation for 20 hours at 37° C. and under aerobic conditions, the blood-agar and the medium of the invention were inoculated using the Todd Hewitt broth and then incubated at 37° C. for 20 h under aerobic conditions.

The confirmation of the colonies suspected of being characteristic of streptococcus B, i.e. that appeared pink/red in color, was carried out by means of an agglutination assay using the Slidex Strepto Kit reagent according to the supplier's recommendations (bioMérieux, France).

Among the 134 samples, 112 were inoculated onto the agar media, firstly, directly from the suspension in physiological saline and, secondly, after enrichment in Todd Hewitt broth. The remaining 22 samples were inoculated onto the agar media only directly from the suspension in physiological saline.

The results, expressed as average percentage sensitivity and specificity, are presented in Table 8 below.

TABLE 8

|  | Columbia agar | Invention agar |
| --- | --- | --- |
| Sensitivity | 95 | 100 |
| Specificity | 90 | 99.5 |

The results in Table 8 above show that the medium of the invention, used with clinical samples, makes it possible to improve the sensitivity and the specificity of detection of *Streptococcus agalactiae*. Specifically, 20/20 specimens containing *Streptococcus agalactiae* are detected on the medium of the invention, against 19 on the Columbia medium, and there is just one false + result on the esterase medium, against 24 on the Columbia agar. It can even be noted that the results are better than when the medium was tested with the laboratory strains.

What is claimed is:

1. A method for specifically detecting and identifying *Streptococcus agalactiae* from among other bacteria species having esterase activity in a sample suspected of containing *Streptococcus agalactiae*, the method comprising:

inoculating the sample on a reaction medium comprising:
   at least one synthetic esterase enzymatic substrate selected from the group consisting of halogenated indoxyloctanoate derivatives, halogenated indoxylnonanoate derivatives, and halogenated indoxyldecanoate derivatives that *Streptococcus agalactiae* are incapable of using at less than 18 hours after inoculation, the esterase enzymatic substrate being configured so that bacteria that use the substrate exhibit a detectable modified appearance that is distinguishable from bacteria that have not used the substrate;
   a synthetic non-esterase enzymatic substrate capable of being used by *Streptococcus agalactiae*, the non-esterase enzymatic substrate being configured so that it confers on a colony that uses the non-esterase enzymatic substrate a detectable modified appearance that is distinguishable from the detectable modified appearance when the esterase substrate is used by a colony and from a colony that has not used the non-esterase enzymatic substrate;

wherein:
   *Streptococcus agalactiae* incubated on the reaction medium exhibit a detectable modified appearance that is distinguishable from other bacteria that:
   use the esterase substrate and not the non-esterase substrate; or
   do not use the esterase substrate and do not use the non-esterase substrates; or
   use both the esterase substrate and the non-esterase substrate;
   the esterase and non-esterase enzymatic substrates are present in the reaction medium at a concentration of 10 to 2000 mg/L;
   a bacteria exhibiting a detectable modified appearance attributable to the esterase enzymatic substrate at 18 hours after inoculation indicates that the colony is not of the species *Streptococcus agalactiae*;
   a presence of a colony that does not exhibit a detectable modified appearance attributable to the esterase enzymatic substrate at 18 hours of incubation and exhibits a detectable modified appearance attributable to the non-esterase enzymatic substrate indicates that the sample contains *Streptococcus agalactiae*;
   and the detectable modified appearance is a change of color of the colony that is visualized by the naked eye, or fluorescence of the colony.

2. The method as claimed in claim 1, wherein said non-esterase enzymatic substrate is at least one enzymatic substrate chosen from the group consisting of α-glucosidase substrates, phosphatase substrates, β-cellobiosidase substrates, N-acetylglucosaminidase substrates and β-glucosidase substrates.

3. The method as claimed in claim 2, wherein said non-esterase enzymatic substrate is a phosphatase substrate or an α-glucosidase substrate.

4. The method as claimed in claim 3, wherein said reaction medium further comprises an enzymatic substrate chosen from the group consisting of a β-cellobiosidase substrate, an N-acetylglucosaminidase substrate and a β-glucosidase substrate.

5. The method according to claim 1, wherein the at least one esterase enzymatic substrate is 5-bromo-6-chloro-3-indoxyloctanoate or 5-bromo-4-chloro-3-indoxyloctanoate.

* * * * *